United States Patent [19]

Ikada et al.

[11] Patent Number: 4,873,227

[45] Date of Patent: Oct. 10, 1989

[54] 3',5'-CAMP DERIVATIVES FOR TREATMENT OF CERTAIN TYPES OF SKIN ULCERS

[75] Inventors: Junji Ikada, Uji; Eiko Mano, Tokyo, both of Japan

[73] Assignee: Daiichi Seiyaku Co., Ltd., Tokyo, Japan

[21] Appl. No.: 60,516

[22] Filed: Jun. 11, 1987

[30] Foreign Application Priority Data

Jun. 16, 1986 [JP] Japan ................................. 61-139749

[51] Int. Cl.$^4$ .............................................. A61K 31/70
[52] U.S. Cl. ....................................... 514/47; 514/48; 536/27; 536/28; 536/29
[58] Field of Search ..................................... 514/47, 48

[56] References Cited

U.S. PATENT DOCUMENTS 3,849,553 11/1974 Dea et al. ............................... 514/47
4,369,181 1/1983 Miller et al. ........................... 514/48

Primary Examiner—Ronald W. Griffin
Assistant Examiner—L. Eric Crane
Attorney, Agent, or Firm—Oblon, Spivak, McClelland, Maier & Neustadt

[57] ABSTRACT

A novel therapeutic agent for skin ulcers comprising as its active component adenosine-3',5'-cyclic phosphate or a derivative thereof, and a method for the treatment of skin ulcers by using the agent.

The therapeutic agent is prepared into various forms such as emulsions, ointments and creams, and is externally applied to the affected part.

12 Claims, No Drawings

3',5'-CAMP DERIVATIVES FOR TREATMENT OF CERTAIN TYPES OF SKIN ULCERS

BACKGROUND OF THE INVENTION (1) Field of the Invention

This invention relates to a novel therapeutic agent for skin ulcers.

(2) Description of the Prior Art

As skin ulcers generally mentioned are pressure gangrenes caused from circulation disorders due to pressure suffered for a long period; gangrenes derived from diabetes or cerebral infarction; thermal burns; frostbites; radionecrosis and so on.

These skin ulcers are difficult to be healed once they occur. Treatments currently carried out are internal treatments in which antibiotics, kallikrein, anginin [pyridinol carbamate (Banyu)], nicotinic acid or antiphlogistic protease preparations are administered locally or totally, and surgical treatments in which disinfectants, steroid hormones, antimicrobial preparations and the like are externally applied.

Internal administrations, however, sometimes fail to give an expected improvement because only a part of the administered medicine reaches and acts on the affected part. Besides, they cannot avoid side effects produced. From these reasons, external preparations would be advisable. However, few medicines were known to be effective which could directly act on the skin and heal the affected part. This have had made the treatment of skin ulcers difficult.

SUMMARY OF THE INVENTION

Under the above situation, the present inventors have earnestly carried out studies in order to provide an external preparation effective for healing skin ulcers, and have found that adenosine-3',5'-cyclic phosphate (hereafter may be referred to as "c-AMP") or its derivatives are very effective. The present invention was accomplished based on the above finding.

Accordingly, this invention provides a therapeutic agent for skin ulcers comprising as its active component adenosine-3',5'-cyclic phosphate or a derivative of the cyclic phosphate.

DETAILED DESCRIPTION OF THE INVENTION AND PREFERRED EMBODIMENTS c-AMP derivatives usable in this invention include $N^6$-monoacyladenosine-3',5'-cyclic phosphate, 2'-O-monoacyladenosine-3',5'-cyclic phosphate, $N^6$,2'-O-diacyladenosine-3',5'-cyclic phosphate or their 8-mercapto, 8-lower alkylthi, 8-benzylthio, 8-amino, 8-hydroxy, 8-chloro or 8-bromo substitutions, 8-benzylthioadenosine-3',5'-cyclic phosphate or its $N^6$-lower alkyl substitution or 8-mercaptoadenosine-3',5'-cyclic phosphate. c-AMP and these derivatives are all known compounds which are described in Japanese Patent Publication (Tokkyo Kokoku) No. 22559/1975, "Nippon Rinsho", vol. 40, No. 11, pp 14–19, 1982, Journal of Cyclic Nucleoide Research, 2, pp 307–319(1976) and Biochim. Biophys. Acta, 148 (1967), 99–105.

The therapeutic agents for skin ulcers according to this invention can be prepared into various forms such as solutions, emulsions, ointments, creams, lotions, poultices and the like by incorporating c-AMP or its derivatives into a base. As to the base, any known base materials are usable. Preferable preparations are solutions obtained by dissolving c-AMP or its derivatives in a physiological saline solution and ointments using macrogol as a base. The amount of c-AMP or its derivatives to be incorporated is varied in a wide range, and normally, 3 wt % of the quantity of the base is preferable.

The therapeutic agents according to this invention are generally applied to the affected part from once to several times a day, each time in such an amount that c-AMP or its derivatives are contained 3 mg–3 g/100 $cm^2$ and more preferably 50–1000 mg/100 $cm^2$ depending on the degree and area of ulceration.

This invention is now explained in more detail by way of examples, which should not be construed as limiting the invention.

EXAMPLE 1

(1) A solution was prepared by dissolving 300 mg of sodium bucladesinate ($N^6$,2'-O-dibutyryladenosine 3',5'-cyclic sodium phosphate) in 10 mg of physiological saline solution.

(2) An ointment was prepared by using 50 g of Macrogol 4000, 50 g of Macrogol 400 and 3 of sodium bucladesinate by a usual manner.

EXAMPLE 2

A 60 year old male patient who was diagnosed pyoderma gangrenosum in the lower part of the left thigh was treated with various ointments, pig skin applications, intravenous drip and the like, but there were no significant improvements observed.

This patient was then treated with 5 mg sodium bucladesinate solution (content of sodium bucladesinate: 150 mg) obtained in Example 1 (1) which was soaked in guaze and applied to the affected part once a day. A few days later, the ulceration area was observed to be reduced, and about 2 months later, the ulceration was completely epithelializated and healed.

EXAMPLE 3

Several ulcers shown in Table 1 were treated using an ointment of sodium bucladesinate obtained in Example 1 (2). In each case, the ointment was applied to the affected part in such an amount that sodium bucladesinate was contained 50–1000 mg/100 $cm^2$.

The results are also shown in Table 1. The data indicate excellent therapeutic effects for all cases. In the table, the letter "w" means week.

TABLE 1

| Name | Sex | Age | Diagnosis | Basic Disease | Suffering Period | Prior Treatment | Symptoms | Administration Period | Progress | Side Effects | Effectiveness |
|---|---|---|---|---|---|---|---|---|---|---|---|
| I. M. | f | 86 | Decubitus | Cervical carcinoma | About 1 month | About 1 month treatment by Gentacin ointment [gentamicin $C_{1a}$ (Schering/Shionogi)] found invalid. | Ulceration with white coverings and faulty granulations in the lumbar region. | 6w | After a few days of administration, the white coverings began to disappear and benign reddish granulations appeared; Ulceration area rapidly reduced to 14.0 (7.0 × 2.0) (1w), 4.5 (3.0 × 1.5) (2w) and 2.76 (2.3 × 1.2) (4w). After 6 weeks, epidermis was formed with thin crust remained partially and almost healed. | None | Very Effective |
| K. K. | f | 72 | Decubitus | Rupture of the bladder; Peritonitis; Fracture of the lumbar vertebrae; Palsy in the left side | 9 months | 2 month treatment by Hibitane cream [chlorhexidine (Sumitomo)], Rinderon A ointment [fradiomycin sulfate, sodium betamethasone phosphate (Shionogi)] found invalid. 7 month treatment by Solcoceryl [deproteinized extract obtained from hemolysate of calves (Tobishi)], Isalopan ointment [aluminum chloroxy allantoinate (Grelan/Takeda)], Stable Trypure [trypsin (Kodama)] found invalid. 5 month treatment by Solcoceryl, Elase C [fibrinolysin, deoxyribonuclease (Sankyo)] revealed a little improvement. Thereafter, 1 month treatment by mercurochrome found invalid. | Ulcerations of 420 (20 × 21) in the lumbar region and 110.5 (13 × 8.5) in the femoral region; thigh bone, head thereof and ilac bone are partially exposed and the muscle appears old meat; Strong ischaemia; Systemic conditions very bad, terminal stage. | 4w | After 1 week of administration, granulations turned to hemorrhagic and muscle color to fresh red. After 3 weeks, the ulceration area reduced to 360.0 (18 × 20) in the rear lumbar part and 85.0 (12.5 × 6.8) in the thigh (85.7% and 76.9%, respectively). 4w: Death from basic disease | None | Effective |
| T. I. | m | 37 | Decubitus | Encephalopathy (Vegetation) | 6 months | | Deep ulceration of 2.7 (1.9 × 1.4) in the lumbar region; Granulations slightly faulty; Wound region tends to tear sideways because the patient strongly presses his lumbar part to the floor when he changes the position of his upper part or lower part due to rigidity. | 7w | After 3w of administration, granulations began to have very good appearance. Ulceration area reduced. 3w: 1.5 (1.9 × 0.8), 6w: 1.0 (2.0 × 0.5), 7w: 0.6 (1.6 × 0.4) = 22.2% | None | Effective |
| Y. M. | m | 57 | Decubitus | Gastric ulcer; Peritonitis; Pulmonary insufficiency | 2w | Treatment by Isodine [povidone iodine (Meiji Seika)], excerbation | Ulceration of 3.7 (1.6 × 2.3) in the lumbar region; Granulations slightly faulty | 4w | After 1w, granulations turned to be dry, no exudate; after 2w, very good conditions; after 4w completely healed. Ulceration area: after 2w, 2.5 (1.3 × 1.9), after 3w; 1.0 (0.9 × 1.1), after 4w, completely healed. 1w of administration brought | None | Very effective |
| | | | | Left cervica | | Geben cream [silver | Ulceration with light | | | | |

TABLE 1-continued

| Name | Sex | Age | Diagnosis | Basic Disease | Suffering Period | Prior Treatment | Symptoms | Administration Period | Progress | Side Effects | Effectiveness |
|---|---|---|---|---|---|---|---|---|---|---|---|
| R. S. | m | 55 | Ulceration from radiation | tumor (squamous cell carcinoma); Hypertension Diabetes | about 2.5 months | sulfadiazine (Tokyo Tanabe)], intractable | yellow gelly substances in the left region of neck | 1w | significant reduction. Before Administration: 2.1 (2.1 × 1.0 cm) 1w: 0.19 (0.95 × 0.2 cm) = 9.0% | None | Very effective |
| R. H. | f | 7 | Ambustion (II) | None | 5w | 5 weeks of treatment by Geben cream, no effect Elase ointment, Gentacin ointment | Ulceration of 1.3 (1.3 × 1.0) in the right-lower thigh Deep ulceration in side region of the right-lower thigh by a foot warmer. Partially blacken with dirty yellow coverings | 2w | After 1w, 0.8 (0.6 × 0.3), dry, no exudate. After 2w, completely healed. 1w: dry, soft black crust removed; Ulceration definitely | None | Very effective |
| H. K. | m | 25 | Ambustion II | None | 2w | external application of Fucidin Leo Intertulle [sodium fusidate (Sankyo)] by other hospital found invalid. Came to this hospital to have skin grafting | | 6w | disappeared and skin grafting considered unnecessary. Prior to Administration: 5.6 (2.8 × 2.0 cm) 1w: 3.8 (2.4 × 1.6 cm) 2w: 1.3 (1.5 × 0.85 cm) 5w: 0.1 (0.4 × 0.2 cm) of erosion 6w: healed | None | Very effective |
| O. S. | f | 52 | Leg ulcer | Iron deficiency anemia | about 2 months | Geben cream found invalid. Elase C found invalid. | Deep ulceration with white coverings in the inside of the left leg; Painful | | 1 day: dried 2 days: circumpherencial erosion healed About 2w: dry crust Strong pain was suffered in the 1st day and the pain decreased from the next day. After 2 weeks, pain almost disappeared. Prior to Administration: 2.5 (1.8 × 1.4 cm) 1w: 1.2 (1.0 × 1.2 cm) 2w: 1.0 (0.9 × 1.1 cm) 4w: 0.4 (0.5 × 0.8 cm), crust 6w: 0.2 (0.4 × 0.55 cm) Returned home but came back to the hospital again due to exacerbation caused by being frequently forced to maintain upright posture at home. | None | Effective |
| H. S. | m | 27 | Frostbite | None | 1w | None | Blisters and blood blisters were formed in legs due to frostbite. No sense at all. Removal of Nercosis epidermis resulted in deep ulceration. | About 8w | 1w: no exudate 2w: very shallow erosion, ulcer area reduced, sense come back again 4w: 1.0 × 0.75 cm 5w: dry erosion 8w: completely healed, normal sensation | None | Very effective |

EXAMPLE 4

Vulnerary effects of sodium bucladesinate and 8-benzylthio-N[6]-butyladenosine-3',5'-cyclic phosphate (hereafter abbreviated to BTBcAMP) were investigated by the following test. The results are shown in Table 2.

TEST METHOD

Several groups of SD male rats (8 weeks old, weighing 225-285 g), each group consisting of three rats, were used. The hair in the abdominal region was removed and then the local skin was excoriated to have a lesion of 3 cm in diameter under etherization to prepare a full-thickness avulsion model. Test samples were sodium bucladesinate and BTBcAMP. They were applied 60 mg each for the first day of the treatment, and 30 mg each for the second and the third day. The samples were applied as they were. The lesion area of each rat was measured after 0, 24, 48 and 72 hours respectively, and an average value of reduction ratio obtained was regarded as reflecting the vulnerary effect.

RESULTS

TABLE 2

| % Reduction in the full-thickness avulsion model | | | | |
| --- | --- | --- | --- | --- |
| Time (hours) | 0 | 24 | 48 | 72 |
| Sample | | | | |
| Control | — | 4.9 | 13.7 | 13.5 |
| Sodium Bucladesinate | — | 2.4 | 12.5 | 20.3 |
| BTBcAMP | — | 15.3 | 17.9 | 21.4 |

From the above data, it is understood that the groups which were treated with sodium bucladesinate and BTBcAMP were rapidly healed compared with Control (No treatment carried out).

What is claimed is:

1. A method for the treatment of a skin ulcer selected from the group consisting of a gangrene, a thermal burn, frostbite and radionecrosis, in mammals, which comprises applying to an affected area of a mammal an effective amount of an adenosine-3',5'-cyclic phosphate derivative of the formula (I):

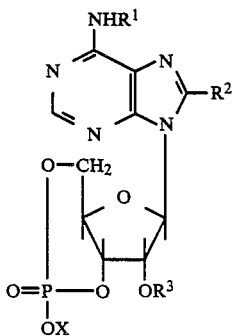

wherein $R^1$ represents a hydrogen atom, an alkyl group of from 1 to 6 carbon atoms or an aliphatic acyl group of from 2 to 7 carbon atoms; $R^2$ represents a hydrogen atom, a mercapto group, an alkylthio group of from 1 to 6 carbon atoms, a benzylthio group, an amino group, a hydroxy group, a chlorine atom or a bromine atom; $R^3$ represents a hydrogen atom or an aliphatic acyl group of from 2 to 7 carbon atoms; with the proviso that not all of $R^1$, $R^2$ and $R^3$ are a hydrogen atom at the same time, and X represents a hydrogen atom or a sodium atom, to the affected portion.

2. The method according to claim 1, wherein both $R^1$ and $R^3$ are an n-butyryl group, $R^2$ is a hydrogen atom, and X is a sodium atom.

3. The method according to claim 1, wherein $R^1$ is an n-butyl group, $R^2$ is a benzylthio group, $R^3$ is a hydrogen atom and X is a sodium atom.

4. A method for the treatment of a disease selected from the group consisting of decubitus, ulceration from radiation, ambustion, leg ulcer and frostbite, in mammals, which comprises applying to an affected area of a mammal an effective amount of an adenosine-3',5'-cyclic phosphate derivative of the formula (I):

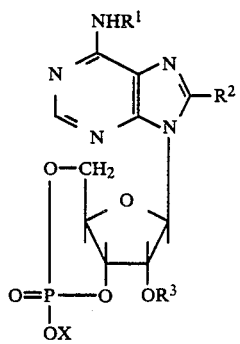

wherein $R^1$ represents a hydrogen atom, an alkyl group of from 1 to 6 carbon atoms or an aliphatic acyl group of from 2 to 7 carbon atoms; $R^2$ represents a hydrogen atom, a mercapto group, an alkylthio group of from 1 to 6 carbon atoms, a benzylthio group, an amino group, a hydroxy group, a chlorine atom or a bromine atom; $R^3$ represents a hydrogen atom or an aliphatic acyl group of from 2 to 7 carbon atoms; with the proviso that not all of $R^1$, $R^2$ and $R^3$ are a hydrogen atom at the same time, and X represents a hydrogen atom or a sodium atom, to the affected portion.

5. The method according to claim 4, wherein both $R^1$ and $R^3$ are an n-butyryl group, $R^2$ is a hydrogen atom, and X is a sodium atom.

6. The method according to claim 4, wherein $R^1$ is an n-butyl group, $R^2$ is a benzylthio group, $R^3$ is a hydrogen atom and X is a sodium atom.

7. A method for the treatment of decubitus which comprises applying to an affected area of a mammal an effective amount of an adenosine-3',5'-cyclic phosphate derivative of the formula (I):

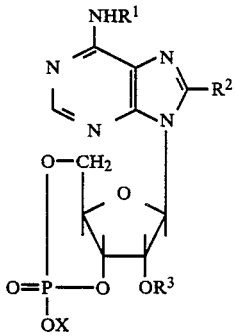

wherein $R^1$ represents a hydrogen atom, an alkyl group of from 1 to 6 carbon atoms or an aliphatic acyl group of from 2 to 7 carbon atoms; $R^2$ represents a hydrogen atom, a mercapto group, an alkylthio group of from 1 to 6 carbon atoms, a benzylthio group, an amino group, a hydroxy group, a chlorine atom or a bromine atom; $R^3$ represents a hydrogren atom or an aliphatic acyl group of from 2 to 7 carbon atoms; with the proviso that not all of $R^1$, $R^2$ and $R^3$ are a hydrogen atom at the same time, and X represents a hydrogen atom or a sodium atom, to the affected portion.

8. A method according to claim 7, wherein both $R^1$ and $R^3$ are an n-butyryl group, $R^2$ is a hydrogen atom, and X is a sodium atom.

9. The method according to claim 7, wherein $R^1$ is a n-butyl group, $R^2$ is a benzylthio group, $R^3$ is a hydrogen atom and X is a sodium atom.

10. A method for the treatment of pressure gangrene in mammals, which comprises applying to an affected area of a mammal an effective amount of an adenosine-3',5'-cyclic phosphate derivative of the formula (I):

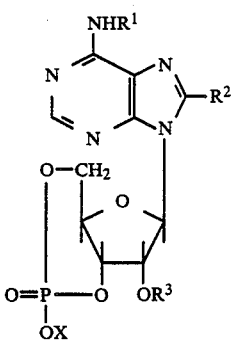

wherein $R^1$ represents a hydrogen atom, an alkyl group of from 1 to 6 carbon atoms or an aliphatic acyl group of from 2 to 7 carbon atoms; $R^2$ represents a hydrogen atom, a mercapto group, an alkylthio group of from 1 to 6 carbon atoms, a benzylthio group, an amino group, a hydroxy group, a chlorine atom or a bromine atom; $R^3$ represents a hydrogen atom or an aliphatic acyl group of from 2 to 7 carbon atoms; with the proviso that not all of $R^1$, $R^2$ and $R^3$ are a hydrogen atom the same time, and X represents a hydrogen atom or a sodium atom, to the affected portion.

11. The method according to claim 10, wherein both $R^1$ and $R^3$ are an n-butyryl group, $R^2$ is a hydrogen atom and X is a sodium atom.

12. The method according to claim 10, wherein $R^1$ is an n-butyl group, $R^2$ is a benzythio group, $R^3$ is a hydrogen atom and x is a sodium atom.

* * * * *

UNITED STATES PATENT AND TRADEMARK OFFICE
CERTIFICATE OF CORRECTION

PATENT NO. : 4,873,227

DATED : OCTOBER 10, 1989

INVENTOR(S) : JUNJI IKADA, ET AL

It is certified that error appears in the above-identified patent and that said Letters Patent is hereby corrected as shown below:

Column 1, line 53, change "alkylthi" to --alkylthio--.

Column 2, line 3, change "Nucleoide" to --Nucleotide--.

Column 10, line 24, after "atom" insert --at--.

Signed and Sealed this

Fifth Day of November, 1991

Attest:

HARRY F. MANBECK, JR.

*Attesting Officer*   *Commissioner of Patents and Trademarks*